United States Patent [19]

Drago et al.

[11] Patent Number: 4,538,011
[45] Date of Patent: Aug. 27, 1985

[54] METHOD FOR THE PREPARATION OF HALOGEN SUBSTITUTED METHANES AND ETHANES

[75] Inventors: Russell S. Drago, Gainesville, Fla.; James G. Miller, Nyack, N.Y.; Keith D. Weiss, Gainesville, Fla.

[73] Assignee: University of Florida, Gainesville, Fla.

[21] Appl. No.: 603,301

[22] Filed: Apr. 24, 1984

[51] Int. Cl.³ .............................................. C07C 17/00
[52] U.S. Cl. .................................................... 570/240
[58] Field of Search ......................................... 570/240

[56] References Cited

U.S. PATENT DOCUMENTS 4,041,087  8/1977  Vannice .............................. 570/240

Primary Examiner—Anton H. Sutto
Assistant Examiner—Joseph A. Boska
Attorney, Agent, or Firm—Dennis P. Clarke

[57] ABSTRACT

Method of preparing methyl halides over mixtures of methyl halides with halogenated ethanes by reaction between carbon monoxide, hydrogen and a hydrogen halide in the presence of a metal carbonyl complex catalyst at a temperature below 200° C.

37 Claims, No Drawings

4,538,011

METHOD FOR THE PREPARATION OF HALOGEN SUBSTITUTED METHANES AND ETHANES

This invention was made with government support under CHE-82-13398 awarded the National Science Foundation. The government has certain rights in this invention.

FIELD OF THE INVENTION

The present invention relates to a method for the preparation of methyl halides or mixtures of methyl halides and haloethanes by the reaction between carbon monoxide and hydrogen (synthesis gas) and a hydrohalide in the presence of a catalyst under mild conditions.

BACKGROUND OF THE INVENTION

Currently, two principal methods are employed industrially for the synthesis of methyl halides. One method involves the chlorination of methane and the other relies on the reaction between methanol and a hydrogen halide. The latter process is the most widely employed and accounts for most of the methyl chloride production in the world. This method produces methyl halide as the sole product of reaction whereas the halogenation of methane typically yields mixtures of methyl halide, methlyene halide, haloform and carbon tetrahalide.

Both of these procedures, however, require the utilization of relatively high temperatures and, typically, high pressures, to achieve acceptable yields. These rigorous reaction condition requirements necessitate the use of expensive equipment and not infrequent shutdowns for repair and replacement thereof due to the deleterious effects of hydrogen halide thereon at elevated temperatures. Such necessary demands on the system used for synthesis of the methyl halides contribute to the high cost of methyl halide in the marketplace.

U.S. Pat. No. 4,041,087 describes a method for the preparation of halogenated hydrocarbons, including methyl halides, by reacting carbon monoxide, hydrogen and a source of halogen in the presence of a particular catalyst at temperatures from 200° to 1000° C., preferably 200°–700° C. and at pressures from 0.1 to 500 atm, most preferably 1–10 atm. In the examples of preferred embodiments set forth in the patent, temperatures of 270° C. and above are employed. The catalyst is described as one of several specific Group VIII metals or alloys (rhenium, platinun-iridium and platinum-rhenium) in combinations with an acidic inorganic oxide material.

Although the patented method represents a new approach to the preparation of halogenated hydrocarbons, it also requires the utilization of substantially the same rigorous conditions employed in typical prior art methods. As a result, the costs of halogenated hydrocarbons produced according to the patented method remain relatively high.

It is an object of the present invention to provide a method for the preparation of methyl halide and mixtures thereof with halogenated ethanes which can be carried out at much lower temperatures and under milder conditions than utilized heretofore thereby resulting in substantial cost savings.

SUMMARY OF THE INVENTION

The present invention is predicated on the discovery that excellent yields of methyl halides ($CH_3X$) and mixtures of methyl halides and haloethanes ($XCH_2$-$CH_3$), wherein X is chlorine, bromine, fluorine or iodine, respectively, may be produced by contacting CO, $H_2$ and HX at a temperature below 200° C. in the presence of a catalytic amount of a metal carbonyl complex capable of oxidatively adding hydrogen or HX having the formula $M_n(CO)_m$ wherein M is a transition metal, n and m may be the same or different and are integers having a value of at least 1, in association with (1) at least one Lewis or Brönsted acid capable of coordinating the oxygen atom of said carbonyl moiety and (2) at least one Lewis base other than CO attached to the metal of the metal carbonyl complex capable of activating hydrogen or a metal carbonyl complex having the formula $Z_y[M_n(CO)_m{}^{y-}]$ wherein M, n and m have the meanings set forth above, y is an integer having a value of at least 1 and Z is a cation or a cationic support ionically bonded to or in association with the transition metal anion.

Typically, the method produces large amounts of desired product at temperatures between 20° and 100° C. thereby greatly reducing the overall cost of the apparatus and systems required for handling the reactants and conducting the reaction and lessening the cost of the product.

DETAILED DESCRIPTION OF THE INVENTION

Any transition metal complex capable of undergoing an oxidative addition reaction with hydrogen may be utilized in the catalyst composition employed in the method of the invention. Suitable transition metal complexes are those which undergo the oxidative addition reaction with hydrogen as described in Huheey, Inorganic Chemistry, 3d. Ed., pages 654–7, (Harper & Rowe, 1983), the disclosure of which is incorporated herein by reference.

It has been found that the utilization of certain transition metal carbonyls in the catalyst result in the formation of methyl halides as the sole produce whereas the use of other transition metal carbonyls therein favor the formation of mixtures of methyl halides and haloethanes. Thus, $Ir_4(CO)_{11}$-Lewis base functions in the catalyst composition to produce methyl halides predominantly, whereas catalyst compositions made by coordinating Group VIII metal (CO, Ru, Fe, monomeric Ir, Rh, etc.) as well as Re and Mn carbonyls to a Lewis base act to produce mixtures of $CH_3X$ and $XCH_2$-$CH_3$. A catalyst based upon the anion, $Rh_{12}(CO)_{30}{}^2$, functions to produce $XCH_2$-$CH_3$ predominantly. The precise reason for the dichotomy of results depending upon the identity of the transition metal is not completely understood.

The combination of a transition metal carbonyl complex, Lewis or Brönsted acid and Lewis base enables the method to be conducted under much milder conditions than in the case where one or more of the components is omitted. Although it is to be understood that the invention is not bound by any mechanism of operation, it is theorized that simultaneous coordination of the carbon by the transition metal and oxygen by the Lewis or Brönsted acid facilitates the conversion of CO to the alkyl halide.

The transition metal carbonyl-base may simply be admixed with the Lewis or Brönsted acid and Lewis base or bonded to a Lewis or Brönsted acid support material.

Suitable Lewis or Brönsted acids include inorganic oxides, e.g., alumina, silica gel, zeolites or conventional Lewis acids, e.g., aluminum halide (i.e., $AlX_3$).

Where an anionic carbonyl complex is used, i.e., $Z_y[M_n(CO)_m{}^{y-}]$, Z may comprise any suitable cation, e.g., alkali metals, e.g., sodium, potassium, etc.; alkaline earth metals, e.g., magnesium, calcium; tetraalkyl phosphonium; tetraalkyl ammonium, ammonium, etc.

Most preferred are catalyst compositions comprising Lewis acid inorganic metal oxides (e.g., silica, alumina, zeolite, etc.) in the form of catalyst support materials to which is bonded the transition metal carbonyl complex via a Lewis base linkage. The thus bonded material may also be admixed with additional Lewis acid to enhance the catalytic activity thereof.

Suitable Lewis bases include phosphines, e.g., $CH_3P$, $(EtO)_3SiCH_2CH_2P(C_6H_5)_2$, $(C_6H_5)_3P$, etc.

The most preferred transition metal carbonyl precursor for producing methyl halides as substantially the sole alkyl halide product is $Ir_4(CO)_{11}$.

The preferred transition metal carbonyl precursors for producing mixtures of methyl halides and haloethanes are $Ru_3(CO)_{12}$, $Rh_6(CO)_{16}$, $Mn_2(CO)_{10}$ and $Fe(CO)_5$. The preferred transition metal carbonyl anion precursor for a predominant conversion to haloethane is $Rh_{12}(CO)_{30}$.

The catalyst compositions comprising an organic oxide Lewis acid support material to which is bonded the transition metal carbonyl complex via a Lewis base linkage may be prepared according to the methods described by Schrader et al [J. Mol. Catalysis, 9(2), 179-82 (1980)], the disclosure of which is incorporated herein by reference. Briefly, the method involves functionalizing an inorganic metal oxide surface such as silica gel with a Lewis base linking agent such as diphenylphosphine (e.g., betadiphenylphosphineethyltriethoxysilane $[(C_2H_5O)_3SiCH_2CH_2P(C_6H_5)_2]$ and reacting the intermediate product with an appropriate metal carbonyl precursor, e.g., $Ir(CO)_2$ (p-toluidine)Cl, $IrCl_2(C_8H_{12})_2$ diiridium (I), in the presence of carbon monoxide to form, e.g., $Ir_4(CO)_{11}$-base support.

The following reaction scheme typifies the preparative method wherein silica is bonded to an iridium carbonyl complex via a phosphine linkage. It is to be understood, however, that the same general method is applicable for the bonding of any suitable transition metal carbonyl complex to any suitable Lewis or Brönsted acid inorganic metal oxide via a Lewis base linking agent.

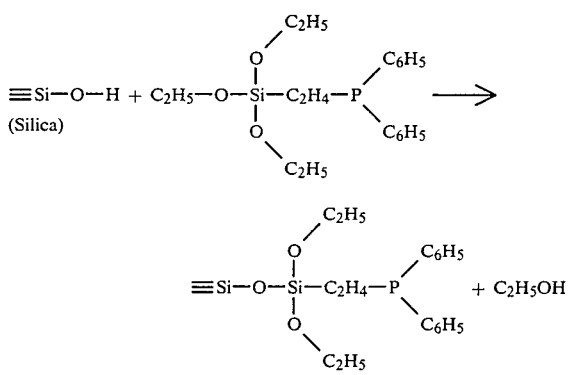

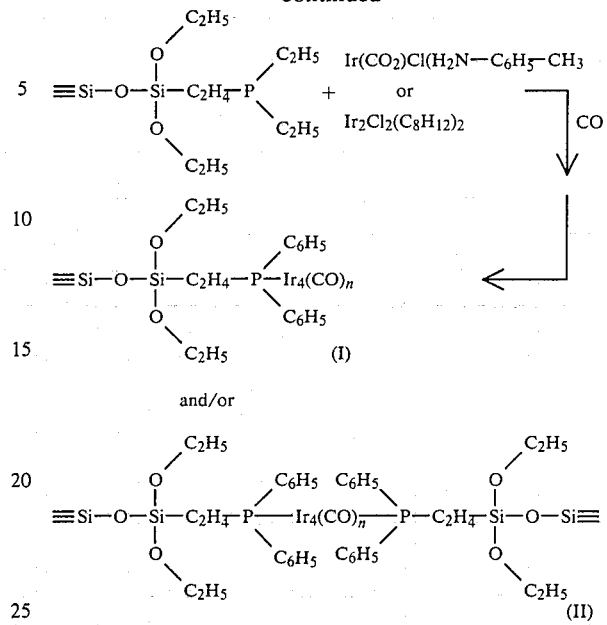

and/or

Alternatively, the metal carbonyl precursor may be reacted with the Lewis base and the inorganic oxide Lewis acid functionalized therewith according to the following scheme:

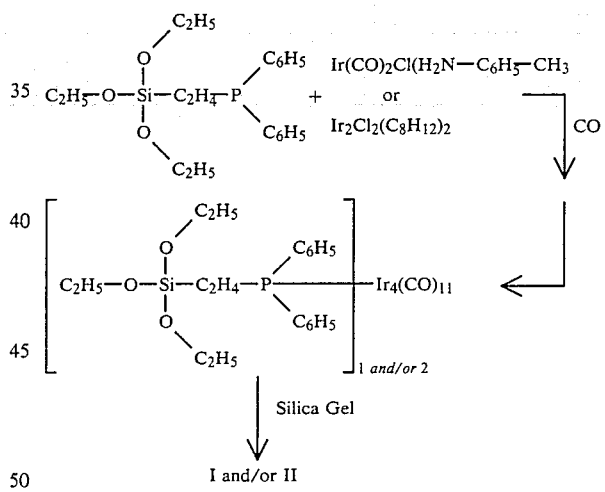

The mono- and di-substituted metal complexes are equally suitable as catalysts in the method of the invention.

Preferably, the method is conducted by passing a mixture of synthesis gas (CO and $H_2$) and HX in a closed reactor over a bed or column of the transition metal carbonyl complex in association with the Lewis acid and Lewis base at a temperature below 200° C., most preferably below about 100° C., at ambient pressure. Any suitable apparatus or system such as those conventionally used for the conversion of synthesis gas may be used in carrying out the method of the invention. See for example the system depicted in Schrader et al, supra.

The method of the invention is applicable for the formation of $CH_3X$ or mixtures of $CH_3X$ and $XCH_2CH_3$ wherein X is chlorine, bromine, fluorine or iodine.

Catalyst compositions comprising the transition metal carbonyl complex bonded to the Lewis acid inorganic metal oxide are preferably those of the formula:

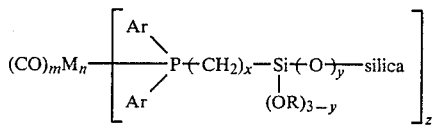

wherein:
M is the transitional metal,
Ar is an aryl hydrocarbyl group,
R is hydrogen or a hydrocarbyl group,
x is an integer greater than or equal to 1
y is an integer from 1 to 3,
z is an integer from 1 to 2,
m is an integer greater than or equal to 1
n is an integer greater than or equal to 1

Any amount of catalyst composition which will catalytically support the reaction may be employed. Moreover, the ratio of $H_2$ to CO to HX is not overly critical. It is only necessary that stoichiometrically equivalent amounts of reactants be present to sustain the reaction.

EXAMPLE 1

A catalyst compositon of the formula

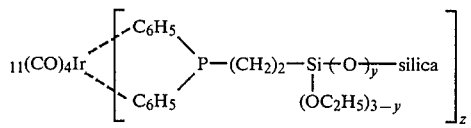

wherein y is 1–3 and z is 1–2 was prepared according to the method of Schrader et al, supra, as follows:

In a 300 ml round bottom flask equipped with a reflux condenser was placed 5 g of silica gel (dried under vacuum at 325° C. for 4 hrs) and 100 ml 3:1 benzene: dioxane solution. After purging the system with $N_2$, 0.45 ml of 2-(diphenylphosphino)-ethyltriethoxysilane was then syringed into the flask. The mixture was refluxed while stirring for ~12 hrs. The solution was filtered in a $N_2$ filled glove bag and washed with benzene, then dried under vacuum at 25° C. for 24 hrs.

In an inert atmosphere box a degassed solution of 76.5 ml 2-methoxyethane and 2.7 ml $H_2O$, 0.055 g $Ir(CO)_2Cl$ (P-toluidine) and 18 g of acid washed mosey zinc and the functionalized silica gel was placed in a pressure reactor. The system was purged 5x's with 55 psi Ar followed by purging with 55 psi CO 5x's. Under 55 psi CO the vessel was heated to 90° C. while stirring for 24 hrs. The reactor was cooled, pressure released and the solution filitered under an inert atmosphere. The functionalized support was then washed with THF and dried under vacuum for 24 hrs at 25° C.

About 1.2 g of the catalyst composition was loaded into a glass flow reactor and purged with CO. The gas stream flowing through the catalyst was modified by the addition thereto of hydrogen, carbon monoxide and HCl to provide a gas flow having the composition: $3H_2:1CO:1HCl$. The gas mixture was allowed to flow through the catalyst at room temperature. Gas chromatographic analysis of the product stream revealed that the only reaction products were $CH_3Cl$ and $H_2O$.

The temperature of the catalyst/reaction zone was increased to 100° C. which resulted in a greater than 100-fold increase in the conversion to $CH_3Cl$.

EXAMPLE 2

A catalyst composition of the formula:

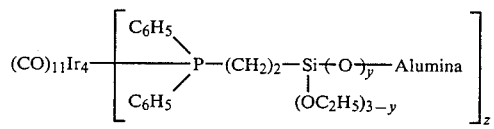

wherein y is 1–3 and z is 1–2 was prepared according to the method of Schrader et al as follows:

In a 300 ml flask equipped with a condenser was placed 10 g of alumina (dilute HCl washed, dried 12 hrs at 80°–90° C.) and 250 ml xylenes. The system was purged with $N_2$ for ½ hr and the 1.5 ml 2-(diphenylphosphino)ethyltriethoxysilane was added by syringe. The mixture was heated to reflux while stirring for 12 hrs, hrs, cooled, filtered and washed with xylenes, toluene and ethanol. Support was then dried in an oven at 100° C. for 12 hrs.

In an inert atmosphere box a degassed solution of 76.5 ml 2-methoxyethanol and 2.7 ml $H_2O$, 0.056 g $Ir(CO)_2Cl$ (p-toluidine), 18.0 grams mosey zinc and 3.0 g of the functionalized alumina support was placed in a pressure reactor. The system was purged 5x's with 55 psi Ar followed by purging with 55 psi CO 5x's. Under 55 psi CO the vessel was heated to 90° C. while stirring for 24 hrs. The reactor was cooled, pressure released and the solution filtered under an insert atmosphere. The functionalized support was then washed with THF and dried under vacuum for 24 hrs at 25° C.

The resulting catalyst was employed in the method of Example 1 and similar reactivity and improved selectivity observed. The system was run for 3 days, shut down for two weeks and re-initiated with no apparent decrease in activity of the catalyst.

EXAMPLE 3

The method of Example 1 was repeated utilizing the catalyst composition thereof mixed with $Al_2Cl_6$ and flowing only a mixture of CO and $H_2$ in a 1:3 ratio therethrough. Only $CH_3Cl$ and $H_2O$ were produced until the chlorine supplied by the $Al_2Cl_6$ was exhausted. When HCl was added to the inflowing gas stream, $CH_3Cl$ was again produced as the sole organic reaction product.

EXAMPLE 4

$Ir_4(CO)_n$ was physically absorbed in silica gel and $Al_2O_3$ according to the following procedure:

Placed in a 100 ml round bottom flask were 0.072 g $Ir_4(CO)_{12}$, 2 grams of silica gel and 50 ml cyclohexane. The mixture was stirred for 3 hrs and solvent removed under vacuum at 25° C. The composition was dried under vacuum for 6 hrs at 25° C. (theoretically 2.5% Ir) and utilized in the method of Example 1. No catalytic activity was observed below 100° C. Between 100° and 150° C. the catalyst turned grey which suggested the conversion of the carbonyl to metal crystallite. A mixture of products consisting of $CH_4$, $CH_3Cl$ and other unidentified materials was obtained at the elevated temperatures.

EXAMPLE 5

$(C_6H_5)_3PIr_4(CO)_{11}$ was prepared according to the procedure described by Stuntz et al, Inorganic Chemistry, Vol. 15, p. 1994 (1976), the disclosure of which is incorporated herein by reference. The catalyst, 0.0129 g was admixed with 3.5 g of $Al_2Cl_6$ and the resulting composition used as a catalyst in the procedure of Example 1. $CH_3Cl$ was produced as the sole organic reaction product at room temperature. The reaction rate increased up to the melting point of the catalyst (140° C.) at which temperature a variety of products, including $CH_4$, were produced.

EXAMPLE 6

$(C_2H_5O)_3Si-(CH_2)_2-P(C_6H_5)_2Ir_4(CO)_{11}$, (prepared by the procedure described in Example 1) was mixed (0.1 g) with 4.0 g $Al_2Cl_6$ and the mixture utilized as a catalyst in the procedure of Example 1. $CH_3Cl$ was produced as the sole organic product at room temperature. The reaction rate increased up to the melting point of the mixture (140° C.) resulting in the production before melting of a mixture of diverse products, including methane.

EXAMPLE 7

The procedure of Example 1 was repeated utilizing HBr in place of HCl. $CH_3Br$ was produced as the sole organic reaction product.

EXAMPLE 8

To a refluxing mixture of silica gel (1.1 grams) and 125 ml of toluene was added 0.0013 moles of $(OEt)_3SiC_2H_4PPh_2$. After several hours 0.10 grams of $Co_2(CO)_8$ was added to the refluxing and stirred solution. After an additional several hours the solution was filtered and the silica gel collected. This silica gel was then heated in a water bath under $N_2$ at 69° C. for 24 hours to yield $Co_2(CO)_8$-phosphine-silica gel catalyst composition.

The resulting product (0.5 g) was utilized as the catalyst material in the procedure of Example 1. A mixture of $CH_3Cl$ and $ClCH_2$-$CH_3$ (ratio of about 1 to 10, by weight) was produced at 60° C. as the sole organic reaction products.

EXAMPLE 9

To a refluxing mixture of silica gel (1.06 g) and 125 ml of toluene was added 0.0013 moles of $(OEt)_3SiC_2H_4PPh_2$. After several hours 0.16 grams of $Re_2(CO)_{10}$ was added to the refluxing and stirred solution. After an additional several hours of reaction time the solution was filtered and the silica gel collected and dried under vacuum for 24 hours to yield a $Re_2(CO)_{10}$-phosphine-silica gel catalyst composition.

The product (0.7 g) was utilized as a catalyst in the method of Example 1. At room temperature, a mixture of $CH_3Cl$ and $ClCH_2$-$CH_3$ (ratio about 1:1, by weight) was produced as the sole organic reaction product. Elevated temperatures shifted the ratio of products in favor of $C_2H_5Cl$.

EXAMPLE 10

To a refluxing mixture of 0.16 grams of $Ru_3(CO)_{12}$ in 125 ml toluene was added 0.0013 moles of $(OEt)_3SiC_2H_4PPh_2$. After several hours 1.00 grams of silica gel was added. After several additional hours the solution was filtered, the silica gel collected and dried under vacuum for 24 hours to yield a $Ru_3(CO)_{12}$-phosphine-silica gel product.

The product (0.8 g), was utilized as a catalyst in the method of Example 1. At room temperature the sole organic product consisted of mainly $CH_3CH_2Cl$ and some $CH_3Cl$.

Elevated temperatures (>60° C.) led to a color change in the catalyst and an almost exclusive formation of $CH_3CH_2Cl$ up to about 100° C. Above 100° C. a wide variety of products was formed.

EXAMPLE 11

To a refluxing mixture of silica gel (1.09 g) and 125 ml of toluene was added 0.0013 moles of $(OEt)_3SiC_2H_4PPh_2$. After several hours 0.10 grams of $Mn_2(CO)_{10}$ was added to the refluxing and stirred solution. After several additional hours the solution was filtered, the silica gel collected, and dried under vacuum for 24 hours to yield $Mn_2(CO)_{10}$-phosphine-silica gel product.

The resulting product (0.8 grams) was utilized as the catalyst material in the procedure of Example 1. A mixture of $CH_3Cl$ and $ClCH_2CH_3$ (ratio 3:1, by weight) was produced at room temperature. Elevated temperatures shifted the ratio of products to 1:1.

EXAMPLE 12

To a refluxing mixture of silica gel (1.10 g) and 125 ml of toluene was added 0.0013 moles of $(OEt)_3SiC_2H_4PPh_2$. After several hours 1.5 ml of $Fe(CO)_5$ was added to the refluxing and stirred solution. After several additional hours the solution was filtered and the silica gel collected.

The resulting product, $Fe(CO)_5$-phosphine-silica gel (1.1 grams), was utilized as the catalyst material in the procedure of Example 1. At room temperature, a mixture of $CH_3Cl$ and $ClCH_2CH_3$ (ratio 1:2, by weight) was produced as well as several other unidentified products of equal intensity as $CH_3Cl$. At 60° C. the ratio of $ClC_2H_5$:$CH_3Cl$: other products was 10:1:0.5. Elevated temperatures up to 100° C. shifted the ratio difference in favor of ethyl chloride.

EXAMPLE 13

To a refluxing solution of 125 ml toluene and 1.42 grams alumina was added 0.0013 moles of $(OEt)_3SiC_2H_4PPh_2$. After several hours, 0.08 grams of $Ru_3(CO)_{12}$ was added to the stirred and refluxed solution. After several hours this solution was filtered, the alumina collected and dried under vacuum for 24 hours.

The product, $Ru_3(CO)_{12}$-phosphine-silica gel (0.8 grams), was utilized as a catalyst in the method of Example 1. At 60° C. a mixture of $CH_3Cl$ and $ClCH_2CH_3$ (ratio 1:1, by weight) was produced. At elevated temperatures the amount of both products increased with the ratios staying the same.

EXAMPLE 14

To a refluxing solution of 125 ml toluene and 1.32 grams of silica gel was added 0.0013 moles of $(OEt)_3SiC_2H_4PPh_2$. After several hours 0.07 grams of $Rh_6(CO)_{16}$ was added to the stirred, refluxed solution. After several additional hours, the solution was filtered, the silica gel collected and dried under vacuum for 24 hours.

The product, $Rh_6(CO)_{16}$-phosphine-silica gel (0.8 grams), was utilized as a catalyst in the method of Example 1. At room temperature a small amount of $CH_3Cl$ and C₂H₅Cl was produced in a ratio of 1:3, by weight. At elevated temperatures a large increase in the ratio favoring C₂H₅Cl was observed.

EXAMPLE 15

Silica gel functionalized with 3-aminopropyltriethoxy silane and converted to a quaternary ammonium salt was anion exchanged with Na₂Rh₁₂(CO)₃₀.

The resulting proudct (0.7 grams) was utilized as the catalyst material in the procedure of Example 1. At room temperature CH₃Cl and ClCH₂CH₃ was produced. The product ratio showed a greater than 60-fold excess of ethyl chloride as compared to CH₃Cl.

What is claimed is:

1. A method for the preparation of CH₃X or a mixture of CH₃X and XCH₂-CH₃, wherein X is a halogen selected from the group consisting of chlorine, bromine, fluorine and iodine, comprising contacting CO, H₂ and HX at a temperature below 200° C. in the presence of a catalytic amount of a metal carbonyl complex having the formula M$_n$(CO)$_m$, wherein M is a transition metal, n and m are the same or different and represent integers having a value of at least 1, said complex being capable of oxidatively adding H₂ or HCl and further being in association with (1) at least one Lewis or Brönsted acid capable of coordinating the oxygen atom of said carbonyl moiety and (2) at least one Lewis base other than CO attached to the metal atom of the metal carbonyl complex capable of oxidatively adding hydrogen or HX or a metal carbonyl complex having the formula Z$_y$[M$_n$(CO)$_m$$^{y-}$] wherein M, n and m have the meanings set forth above, y is an integer having a value of at least 1 and Z is a cation or a cationic support ionically bonded to or in association with the transition metal anion.

2. The method of claim 1 wherein said Lewis base complex is admixed with said at least one Lewis or Brönsted acid.

3. The method of claim 1 wherein said complex is bonded to said Lewis acid via a Lewis base linkage.

4. The method of claim 3 wherein said complex is bonded to said Lewis acid via a phosphine linkage.

5. The method of claim 3 wherein said Lewis acid is in the form of a catalyst support material.

6. The method of claim 1 wherein said Lewis acid is an inorganic oxide.

7. The method of claim 1 wherein said Lewis acid is selected from the group consisting of alumina, silica, zeolite and aluminum chloride.

8. The method of claim 1 wherein a mixture of said CO, H₂ and HX are passed over a catalyst consisting essentially of said metal carbonyl-base complex in association with a catalyst support material consisting essentially of said Lewis or Brönsted acid.

9. The method of claim 1 wherein X is Cl.

10. The method of claim 1 wherein X is Br.

11. A method according to claim 1 for preparing CH₃X wherein said transition metal is Ir.

12. The method of claim 11 wherein said metal carbonyl is Ir₄(CO)₁₁.

13. The method of claim 11 wherein said Lewis base is a phosphine.

14. The method of claim 13 wherein said phosphine is triphenylphosphine.

15. The method of claim 11 wherein said metal carbonyl complex is Ir₄(CO)₁₁.P(C₆H₅)₃ and said Lewis acid is Al₂Cl₆.

16. The method of claim 11 wherein said transition metal carbonyl complex is bonded to a silica catalyst support material via a Lewis base, said bonded complex having the formula:

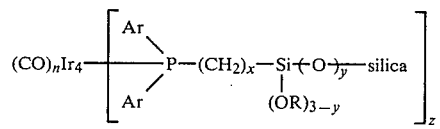

wherein:
Ar is an aryl hydrocarbyl group,
R is hydrogen or a hydrocarbyl group,
x is an integer equal to or greater than 1,
y is an integer from 1 to 3, and
z is an integer from 1 to 2.

17. The method of claim 16 wherein said silica is silica gel.

18. The method of claim 16 wherein said complex bonded to silica gel is also admixed with a Lewis acid.

19. The method of claim 18 wherein said Lewis acid with which said complex bonded to silica gel is admixed is Al₂Cl₆.

20. A method according to claim 1 for preparing a mixture of CH₃S and XCH₂-CH₃ wherein said transition metal is selected from the group consisting of Group VIII metals, Re and Mn.

21. The method of claim 20 wherein said metal carbonyl complex is Co₂(CO)₈.

22. The method of claim 20 wherein said metal carbonyl complex is Re₂(CO)₁₀.

23. The method of claim 20 wherein said metal carbonyl complex is Ru₃(CO)₁₂.

24. The method of claim 20 wherein said metal carbonyl complex is Mn₂(CO)₁₀.

25. The method of claim 20 wherein said metal carbonyl complex is Fe(CO)₅.

26. The method of claim 20 wherein said metal carbonyl complex is Rh₆(CO)₁₂.

27. The method of claim 20 wherein said metal carbonyl complex is IrClP(C₆H₅)₃CO.

28. The method of claim 20 wherein said transition metal carbonyl complex is bonded to a silica catalyst support material via a Lewis base, said bonded complex having the formula:

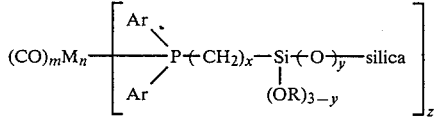

wherein:
m and n have the meanings set forth in claim 1,
M is a Group VIII metal, Mn or Re,
Ar is an aryl hydrocarbonyl group,
R is hydrogen or a hydrocarbyl group,
x is an integer of 1 or greater,
y is an integer of 1 or greater, and
z is an integer from 1 to 2.

29. The method of claim 24 wherein said metal carbonyl complex is Co₂(CO)₈.

30. The method of claim 24 wherein said metal carbonyl complex is Re₂(CO)₁₀.

31. The method of claim 24 wherein said metal carbonyl complex is Ru₃(CO)₁₂.

32. The method of claim 24 wherein said metal carbonyl complex is Mn₂(CO)₁₀.

33. The method of claim 24 wherein said metal carbonyl complex is $Fe(CO)_5$.

34. The method of claim 24 wherein said metal carbonyl complex is $Rh_6(CO)_{12}$.

35. The method of claim 24 wherein said metal carbonyl complex is $IrClP(C_6H_5)_3CO$.

36. The method of claim 20 wherein said Lewis base is a phosphine.

37. The method of claim 28 wherein said phosphine is a triphenyl phosphine.

* * * * *